US010426355B2

(12) United States Patent
Ho

(10) Patent No.: US 10,426,355 B2
(45) Date of Patent: Oct. 1, 2019

(54) INFRARED THERMOMETER

(71) Applicant: Microlife Corporation, Taipei (TW)

(72) Inventor: Chia-Chen Ho, Taipei (TW)

(73) Assignee: MICROLIFE CORPORATION, Taipei (TW)

( * ) Notice: Subject to any disclaimer, the term of this patent is extended or adjusted under 35 U.S.C. 154(b) by 194 days.

(21) Appl. No.: 15/555,371

(22) PCT Filed: May 5, 2015

(86) PCT No.: PCT/CN2015/078251
§ 371 (c)(1),
(2) Date: Sep. 1, 2017

(87) PCT Pub. No.: WO2016/138697
PCT Pub. Date: Sep. 9, 2016

(65) Prior Publication Data
US 2018/0035897 A1     Feb. 8, 2018

(30) Foreign Application Priority Data

Mar. 4, 2015   (CN) .......................... 2015 1 0095691

(51) Int. Cl.
*G01J 5/00*     (2006.01)
*G01K 1/00*    (2006.01)
(Continued)

(52) U.S. Cl.
CPC ................ *A61B 5/01* (2013.01); *G01B 7/003* (2013.01); *G01J 5/0025* (2013.01); *G01J 5/021* (2013.01);
(Continued)

(58) Field of Classification Search
USPC .................................. 374/121, 120, 208, 45
See application file for complete search history.

(56) References Cited

U.S. PATENT DOCUMENTS

| 5,760,593 A | 6/1998 | Lawrence et al. |
| 7,414,415 B2 | 8/2008 | Elliott |

(Continued)

FOREIGN PATENT DOCUMENTS

| CN | 1856689 A | 11/2006 |
| CN | 101933800 A | 1/2011 |

(Continued)

OTHER PUBLICATIONS

International Search Report for PCT/CN2015/078251, dated Nov. 24, 2015, 6 pages including English translation.

*Primary Examiner* — Mirellys Jagan
(74) *Attorney, Agent, or Firm* — Hamre, Schumann, Mueller & Larson, P.C.

(57) ABSTRACT

An infrared thermometer (10), comprising a handheld part (12) and a head (11) connected to the handheld part (12). The head (11) comprises a bottom shell (112); an infrared sensor (113) configured to measure the temperature of an object to be measured; a holder (114) configured to hold the infrared sensor (113) in the bottom shell (112); a housing (111) configured to accommodate the infrared sensor (113) and the holder (114), and combined with the bottom shell (112); a first conductor (115) arranged on the housing (111); and a second conductor (116) arranged between the first conductor (115) and the handheld part (12) and adjacent to the holder (114) wherein the first conductor (115) and the second conductor (116) are capacitive sensors.

12 Claims, 10 Drawing Sheets

(51) Int. Cl.
*G01N 25/00* (2006.01)
*A61B 5/01* (2006.01)
*G01J 5/02* (2006.01)
*G01J 5/04* (2006.01)
*G01B 7/00* (2006.01)
*G01J 5/08* (2006.01)

(52) U.S. Cl.
CPC ............... *G01J 5/0275* (2013.01); *G01J 5/04* (2013.01); *G01J 5/049* (2013.01); *G01J 5/026* (2013.01); *G01J 5/0846* (2013.01)

(56) References Cited

U.S. PATENT DOCUMENTS

| | | | |
|---|---|---|---|
| 2007/0108050 A1* | 5/2007 | Elliott | G01B 7/14 204/424 |
| 2011/0118623 A1* | 5/2011 | Nakanishi | G01K 13/002 600/549 |
| 2015/0043613 A1* | 2/2015 | Tanaka | G01J 5/0275 374/121 |
| 2016/0157732 A1 | 6/2016 | Tanaka | |

FOREIGN PATENT DOCUMENTS

| | | |
|---|---|---|
| CN | 102112853 A | 6/2011 |
| JP | 2011072639 A | 4/2011 |
| JP | 2012217563 A | 11/2012 |
| WO | 2015019878 A1 | 2/2015 |

\* cited by examiner

INFRARED THERMOMETER

BACKGROUND OF THE INVENTION

1. Field of the Invention

The invention relates to an infrared thermometer.

2. Description of Related Art

The conventional infrared thermometer utilizes an infrared sensor to determine the temperature of an object to be measured by measuring the quantity of infrared radiation emitted from the skin surface of the object to be measured. Due to the limited visual angle of the infrared sensor to detect infrared radiation, the sizes of detected areas measured at different distances will not be the same. Therefore, in order to obtain a correct temperature, the temperature of the object to be measured must be measured at an appropriate predetermined distance from the object. To the contrary, an inappropriate distance (shorter or longer than the predetermined distance) will cause wrong measured temperature. However, holding the infrared thermometer by a hand and placing it at the predetermined distance from the object to be measured is not easy for anyone.

Distance sensor is wildly used in the conventional infrared thermometer to measure the distance between the object to be measured and infrared thermometer. For example, the Japanese patent application published as No. JP2012-217563 discloses a technique to measure the capacitance value with a distance sensor when approaching the object to be measured and to compare the measured capacitance value with a preset capacitance value existing in the infrared thermometer. When the measured capacitance value is equal to the preset one, it is determined that the infrared thermometer has touched the object to be measured and then the infrared sensor starts to detect the quantity of infrared radiation emitted from the object to be measured and thereby calculate the temperature of the object to be measured.

However, such distance sensor which determines the distance by measuring the capacitance value generated when it approaches the object to be measured still has a major disadvantage. Specifically, when the operator of the infrared thermometer holds the thermometer by hand, the basis capacitance value of the distance sensor provided at the head (measuring end) of the infrared thermometer may be changed if the operator's hand is too close to the head of the infrared thermometer. This will cause the capacitance value measured by the distance sensor not suitable to accurately determine the distance from the object to be measured, thereby resulting in an error in temperature measurement. In addition, in case of an infrared thermometer which can automatically start measurement, i.e. an infrared thermometer capable of automatically starting up the infrared sensor to measure the temperature once it is determined to be located at an appropriate measuring distance, the infrared sensor may wrongly determine that the object to be measured is approaching due to the distance sensor detecting the capacitance of the conductor nearby when the infrared thermometer is approaching a conductor nearby, for example the infrared thermometer being placed on a metal table, thereby automatically starting the measurement of infrared radiation, which is a wrong activation of the infrared thermometer. In this case, an incorrect measured temperature may be obtained.

In order to solve the problems encountered by the above known techniques, the present invention provides an infrared thermometer which can reduce the influence of capacitance detected from an object not desirable to be measured or from a specific surface that is going to be measured in order to improve the measurement accuracy of the distance. Optionally, the infrared thermometer according to the present invention can take the initiative to determine whether or not there is a conductor which is not desirable to be measured approaching to the infrared thermometer, thereby preventing the infrared sensor of the infrared thermometer from being activated wrongly.

SUMMARY OF THE INVENTION

The invention provides an infrared thermometer, comprising a handheld part and a head connected to the handheld part. The head comprises a bottom shell; an infrared sensor configured to measure the temperature of an object to be measured; a holder configured to hold the infrared sensor to the bottom shell; a housing configured to accommodate the infrared sensor and the holder and to be joined to the bottom shell; a first conductor arranged on the housing; a second conductor arranged between the first conductor and the handheld part and adjacent to the holder. The first conductor is configured to determine the distance between the head and the surface of the object to be measured when the surface of the object to be measured is approaching to the head; and the second conductor reduces the interference to the first conductor when any object not desirable to be measured is approaching to the head.

The first conductor of the above-mentioned infrared thermometer according to the present invention is arranged on an inner or outer surface of the housing.

The second conductor of the above-mentioned infrared thermometer according to the present invention is a shield configured to reduce the interference to the first conductor from the surface of any object not desirable to be measured.

Each of the first and second conductors of the above-mentioned infrared thermometer according to the present invention is a conductive plate.

The second conductor of the above-mentioned infrared thermometer according to the present invention generates a second signal for not activating the infrared sensor to measure the temperature. The infrared thermometer further comprises a microcontroller configured to activate or inactivate the infrared sensor to measure the temperature based on a first and second signals. The first conductor generates the first signal because of the capacity effect formed when approaching to the surface of the object to be measured. The microcontroller then converts the first signal representing a capacitance value into a corresponding distance value for determining the distance between the head of the infrared thermometer and the object to be measured. The microcontroller will activate the infrared sensor to measure the temperature of the object once the distance value falls within the preset range of the distance value. The second conductor generates the second signal because of the capacity effect formed when approaching to the surface of the object not desirable to be measured. When the capacitance value represented by the second signal exceeds a threshold value, the microcontroller will inactivate the infrared sensor.

The preset range of the distance value of the above-mentioned infrared thermometer according to the present invention is between 3 to 5 centimeters.

The first and second conductors of the above-mentioned infrared thermometer according to the present invention are formed of a conductive material, for example, copper, silver, or carbon material.

In the first embodiment of the present invention, the second conductor of the above-mentioned infrared thermometer surrounds a bottom surface and at least one side surface of the holder.

In the second embodiment of the present invention, the second conductor of the above-mentioned infrared thermometer surrounds the bottom surface and at least one side surface of the holder and further comprises an upright plate placed between the holder and the handheld part.

In the third embodiment of the present invention, the second conductor of the above-mentioned infrared thermometer is arranged adjacent to the bottom surface of the holder.

In a fourth embodiment of the present invention, the second conductor of the above-mentioned infrared thermometer is arranged adjacent to the bottom surface of the holder and further comprises an upright plate placed between the holder and the handheld part.

In the fifth embodiment of the present invention, the second conductor of the above-mentioned infrared thermometer is an annular plate surrounding the bottom, side and top surfaces of the holder.

In the sixth embodiment of the present invention, the second conductor of the above-mentioned infrared thermometer is an annular plate surrounding the bottom, side and top surfaces of the holder, and further comprises an upright plate placed between the holder and the handheld part.

In the seventh embodiment of the present invention, the second conductor of the above-mentioned infrared thermometer is an upright plate placed between the holder and the handheld part.

In the second to sixth embodiments of the present invention, the edge of the second conductor flushes with or exceeds beyond the side of the first conductor.

DETAILED DESCRIPTION OF THE INVENTION

Figure 1:
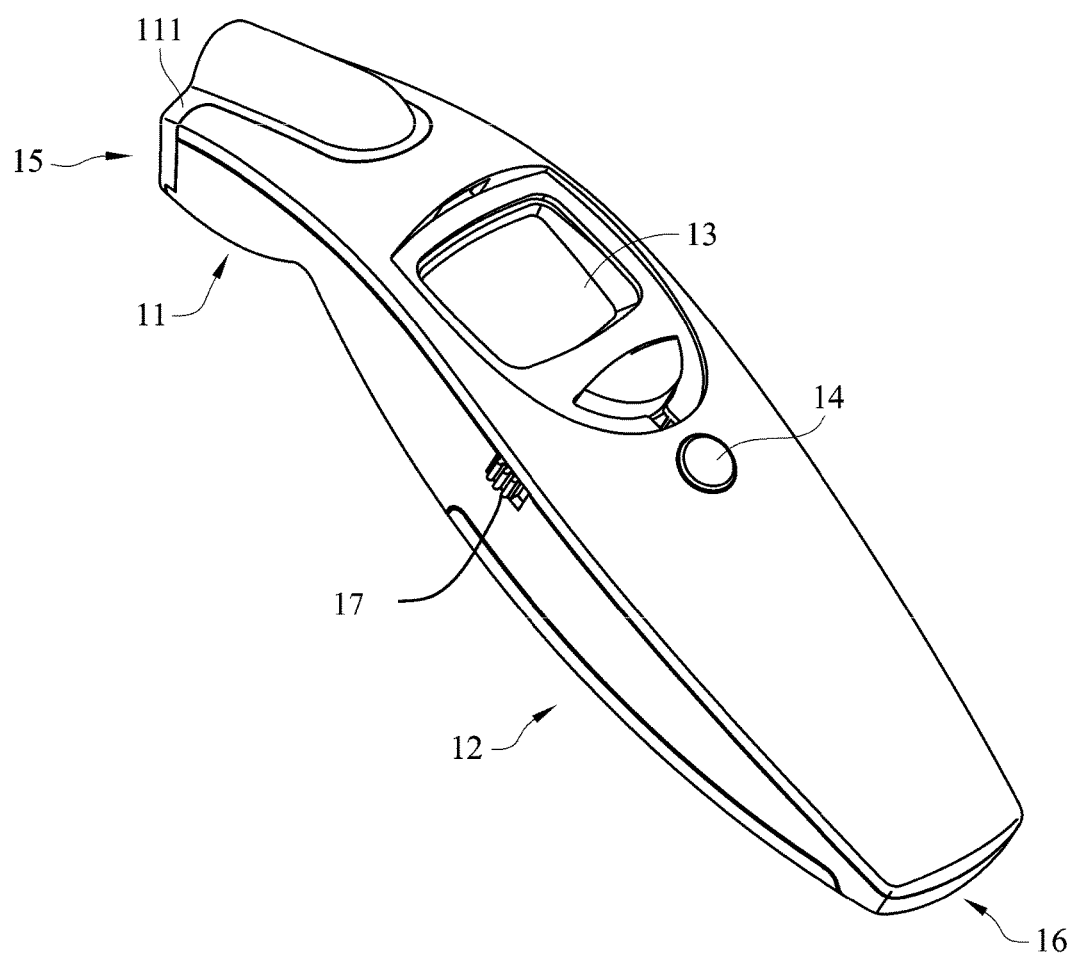
FIG. 1 is a schematic perspective view of an infrared thermometer according to the present invention.

The objects, technical contents, features and efficacy of the present invention will be apparent from the following detailed description of preferred embodiments.

For simplifying and presenting the main content of the present invention, the accompanying drawings show the whole structure of the present invention, but omit the conventional features and corresponding technical descriptions and details thereof to avoid obscuring the claimed scope of the present invention. The same reference numerals in the different drawings denote the same elements.

Figure 2:
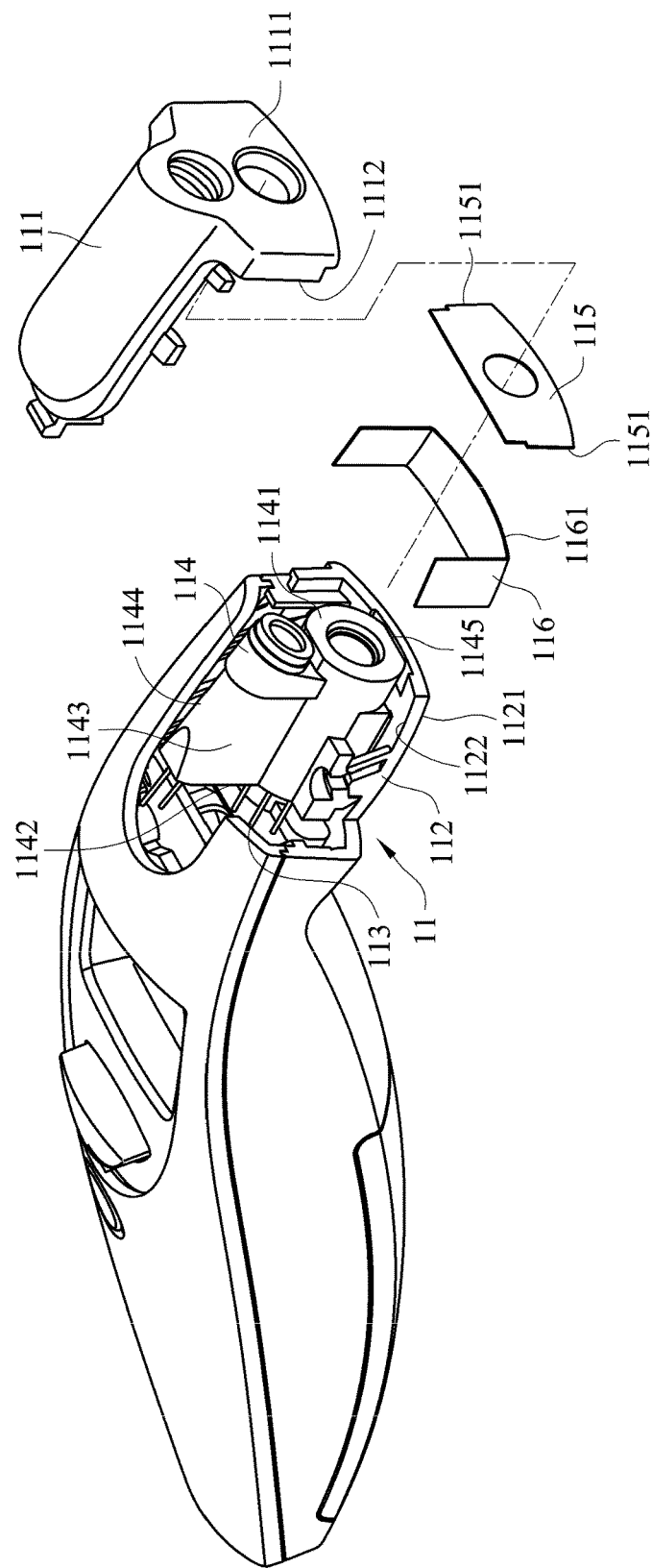
FIG. 2 is an exploded view of the head of the infrared thermometer according to the present invention.
Figure 3:
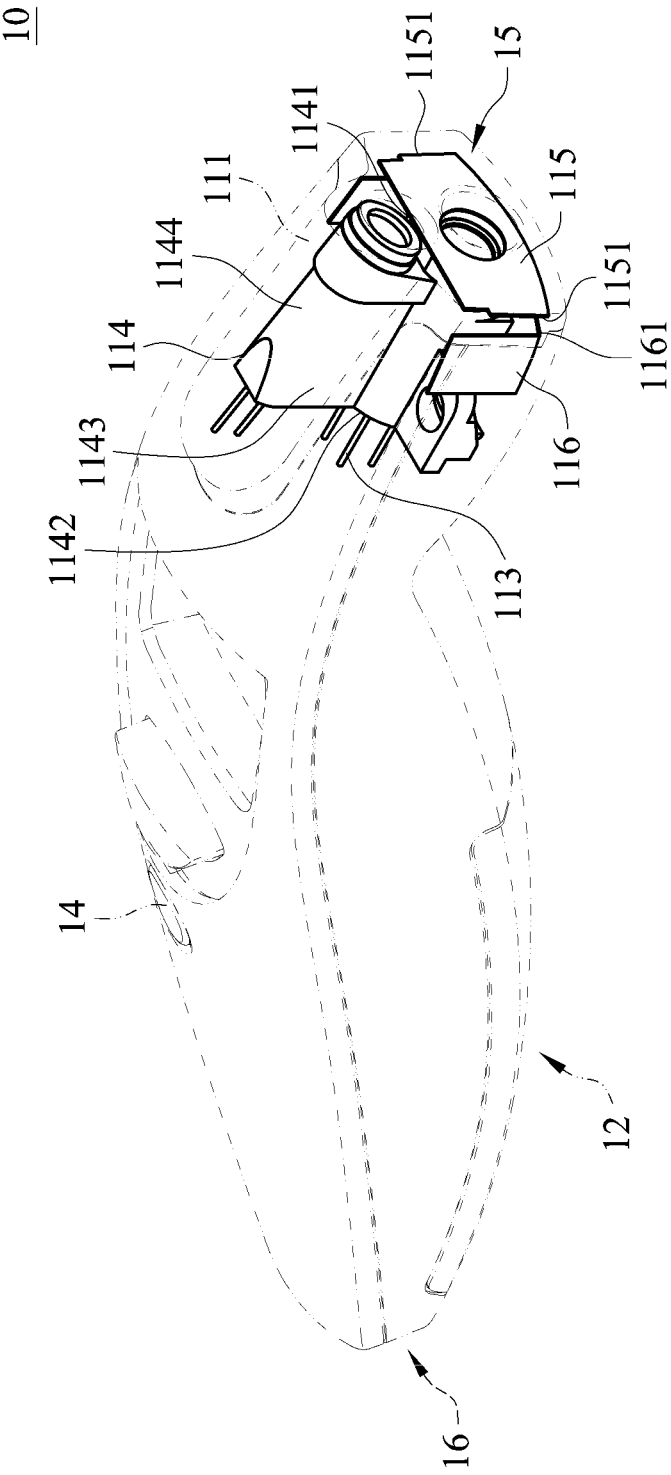
FIG. 3 is a schematic perspective view of the head of the infrared thermometer head according to the first embodiment of the present invention.

FIGS. 1 to 3 illustrate an embodiment of the infrared thermometer according to the present invention, in which a forehead thermometer is exemplified, but the present invention is not so limited, and it should be appreciated that all the devices for measuring temperature by detecting infrared radiation is within the application scope of the present invention. As shown in FIG. 1, the infrared thermometer 10 according to the present invention includes a head 11 and a handheld part 12, and the head 11 and the handheld part 12 are connected to each other. One end of the infrared thermometer 10 proximate to the handheld part 12 is a proximal end 16 of the infrared thermometer, and the other end of the infrared thermometer proximate to the head 11 is a distal end 15 (the end opposite to or away from the handheld part 12) of the infrared thermometer. A power switch 14 is provided on the top surface of the handheld part 12 for turning on or off the power supply of the infrared thermometer 10, but the present invention is not so limited. The power switch 14 of the infrared thermometer 10 may be provided at any position that is accessible to the user. A display 13 may be provided on the top surface of the handheld part 12 for displaying the temperature measured by the infrared thermometer 10 to the user. However, the present invention is not so limited, and a skilled person in the art would know that the display 13 may show a distance value to the user such that the user can decide whether or not the temperature measurement should be started. The display 13 of the infrared thermometer 10 may be provided on any position of the infrared thermometer 10 for user's easy viewing. One side of the infrared thermometer 10 shown in FIG. 1 further includes a switch 17 for switching to a selected mode suitable for measuring the temperature of the object which is desirable to be measured so that the infrared thermometer 10 is switchable for measuring the temperature of the human body or other objects.

As shown in FIG. 2, the head 11 of the infrared thermometer 10 includes an infrared sensor 113, a holder 114, a first conductor 115, and a second conductor 116. The head 11 of the infrared thermometer 10 refers to the measuring end of the infrared thermometer 10 for approaching to the surface of the object to be measured in order to measure the temperature. In the present embodiment, the object to be measured is an article or a living thing, for example, a human body or a patient, and the surface is the forehead surface, but the present invention is not so limited. Those skilled in the art would know that if the object to be measured is an article, such as a milk bottle or the like, then the surface may be the surface of the bottle or the surface of the liquid (e.g., milk). The infrared sensor 113 is a sensor of a conventional forehead thermometer for receiving infrared radiation. Such sensor detects the quantity of infrared radiation emitted from the surface of the object to be measured and converts it into an electronic signal which is then transmitted to the microcontroller (not shown) of the infrared thermometer 10. The microcontroller then converts the electronic signal into a core or shell temperature of the human body based on the data stored in the internal storage of the microcontroller, but the present invention is not so limited. The microcontroller of the present invention may be provided within the handheld part 12 and electronically connected to the infrared sensor 113, the first conductor 115 and the second conductor 116 by wire, but the present invention is not so limited. In other embodiments, the second conductor 116 is grounded and is not electronically connected to the microcontroller.

The holder 114 of the infrared thermometer 10 of the present invention holds the infrared sensor 113 in the head 11. The holder 114 can be shaped into any shape for holding the infrared sensor 113 therein. Turning to FIGS. 2 and 3, the holder 114 of the present invention generally has an irregular shape to hold the infrared sensor 113 or other members in the head 11 of the infrared sensor 113 in place. It should be appreciated that the present invention is not so limited. The holder 114 may be provided in any shape and appearance as long as it is adapted to hold the infrared sensor 113 or other members of the infrared thermometer 10 in the head 11. The holder 114 of the present invention generally has a distal end 1141, a proximal end 1142 (see FIG. 3), two side surfaces 1143 (only one side surface being shown in the drawings), a top surface 1144 and a bottom surface 1145. The distal end 1141 of the holder has the same orientation of the distal end 15 of the infrared thermometer 10. Namely, the distal end is opposite to the handheld part 12 of the infrared thermometer 10. The proximal end 1142 of the holder is opposite to the distal end 1141 of the holder. Namely, the proximal end is opposite to the head 11 of the infrared thermometer 10. The side surfaces 1143 of the holder 114 on both sides of the holder 114 extends between the distal end 1141 and proximal end 1142 of the holder. The two side surfaces 1143 are opposite to each other. The top surface 1144 of the holder 114 extends between the distal end 1141 and proximal end 1142 of the holder and is orthogonal to the side surfaces 1143. The bottom surface 1145 of the holder 114 extends between the distal end 1141 and the proximal end 1142 of the holder and is also orthogonal to the side surface 1143, but the bottom surface 1145 is opposite to the top surface 1144.

The first conductor 115 of the present invention is capable of detecting a capacitance value representing a distance when the head 11 of the infrared thermometer 10 is approaching to the surface of the object to be measured. Specifically, the first conductor 115 acts as a capacitive sensor. The capacitance value is inversely proportional to the distance between the first conductor 115 and the surface of the object to be measured. The first conductor 115 is electronically connected to the microcontroller by a wire and transmits a first signal representing a capacitance value to the microcontroller. The microcontroller then converts the first signal with the sensed capacitance value into a corresponding distance value to determine the distance between the first conductor 115 (thus the infrared sensor 113) and the surface of the object to be measured. When the distance value falls within the range of preset distance values stored in the microcontroller, the microcontroller activates the infrared sensor 113 to measure the temperature of the object to be measured, but the present invention is not so limited. It is also possible to transmit a visual feedback to the display 13 or send an audio feedback to the operator of the infrared thermometer 10 when the distance value falls within the preset distance range in order to indicate that the current distance is suitable for temperature measurement. Accordingly, the operator can start temperature measurement of the infrared sensor 113 of the infrared thermometer 10, for example, by pressing the start button. The preset distance range is between 3 to 5 centimeters. To the contrary, if the detected distance value does not fall within the preset distance range stored in the microcontroller, the temperature measurement of the infrared sensor will not be activated. In this way, it is possible to avoid measuring the temperature when the infrared thermometer is not yet at a suitable distance, thereby improving the accuracy of the temperature measurement of the infrared thermometer 10.

The first conductor 115 is provided on an inner surface 1112 of a housing of the head 11. A person skilled in the art would know that the position of the first conductor 115 is appropriate as long as it is disposed proximate to the distal end 15 of the infrared thermometer 10, i.e., the measuring end, such that the position of the first conductor 115 is just close to the end of the infrared sensor 113. Accordingly, the determination of the distance by the first conductor 115 between the infrared sensor 113 and the surface of the object to be measured will become more accurate.

The first conductor 115 of the present invention may be formed of any suitable conductive material, for example a metal (copper or silver) or carbon. The first conductor 115 may be a thin conductive plate in any shape, preferably a rectangular plate, and more preferably a coating of conductive material coated on the inner surface of the housing of the head of the infrared thermometer 10. It should be appreciated that the first conductor 115 may be provided on the outer surface 1111 of the housing of the head.

The second conductor 116 is provided between the first conductor 115 and the handheld part 12 for the purpose that when the surface of the object not desirable to be measured is approaching to the first conductor 115, the second conductor 116 may act as a shield to reduce the interference to the first conductor 115. This interference may come from an improper electrostatic capacitance generated between the surface of the object not desirable to be measured and the first conductor 115. Using the second conductor 116 as a shield will reduce the electrostatic capacitance caused by the surface of the object not desirable to be measured, so that the capacitance value sensed by the first conductor 115 is as much as possible coming from the surface of the object to be measured so as to improve the accuracy of the distance measurement.

In addition, when the second conductor 116 is electronically connected to the microcontroller, it can be used as an active malfunction prevention sensor. Specifically, when the surface of the object not desirable to be measured is approaching to the second conductor 116, the second conductor 116 has a capacitive effect and generates a second signal. The microcontroller will determine whether or not the capacitance value represented by the second signal exceeds a threshold value preset in the internal storage. If the capacitance value represented by the second signal exceeds the preset threshold value, the microcontroller will not activate the infrared sensor 113 to measure the temperature, or not to give a visual feedback through the display 13 or a sound feedback to the user to indicate the user to start the measurement. This prevents the wrong start-up of the infrared thermometer 10 which happens due to sensing the capacitance value of the incorrect object, and thus the accuracy of temperature measurement can be improved. The second conductor 116 of the present invention may be formed of any suitable metal, or may be a coating coated on the surface of the housing 111 or the surface of bottom shell 112; the metal or coating could be, for example, copper or silver, or carbon or other equivalent conductive material, but the present invention is so limited. The second conductor 116 may be formed of any suitable conductive material. The second conductor 116 may be a conductive plate in any shape.

In the first embodiment of the present invention, as shown in FIG. 3, in addition to the features described above, the second conductor 116 surrounds the bottom surface 1145 and at least one side surface 1143 of the holder 114, preferably two side surfaces 1143. The second conductor 116 is in a U shape when seen from the distal end 15 of the infrared thermometer 10 and abuts the bottom surface 1145 and the side surfaces 1143 of the holder 114. The length of the second conductor 116 extending from the edge 1161 toward the handheld part 12 is approximately one third to full of the length of the holder from the distal end 1141 to the proximal end 1142, preferably from one third to one half, but the present invention is not so limited. The length of the second conductor 116 may be longer than that of the holder 114. The U-shaped second conductor 116 efficiently shields the first conductor from the interference caused by any conductors below or beside the infrared thermometer 10. If the second conductor 116 is electronically connected to the microcontroller and acts as a capacitive sensor, but the present invention is not so limited, it may detect the capacitance value of the capacitance effect from the surface of the object not desirable to be measured, for example operator's (or user's) hand or the surface of a conductive table where the infrared thermometer 10 is placed.

Figure 4:
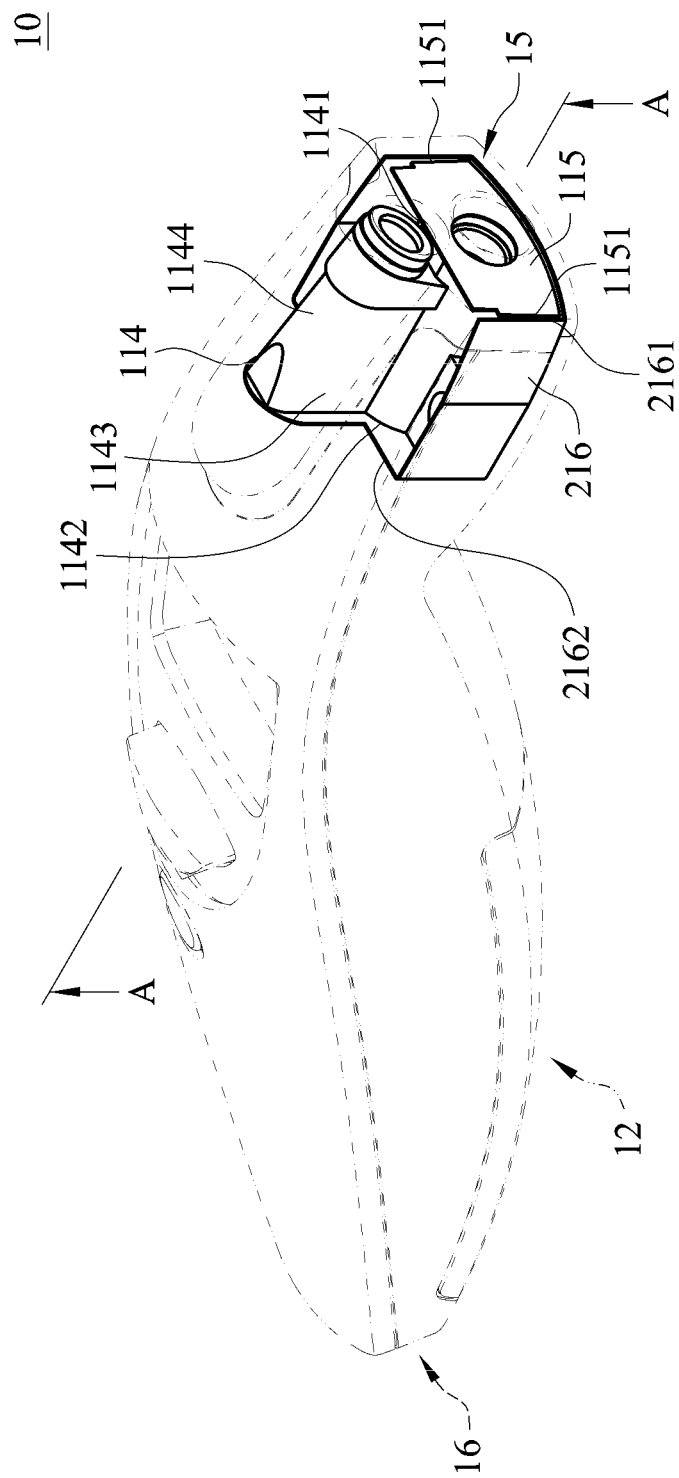
FIG. 4 is a schematic perspective view of the head of the infrared thermometer according to the second embodiment of the present invention.

In the second embodiment of the present invention, as shown in FIG. 4, in addition to the features described above and the features of the first embodiment, the second conductor 216 further includes an upright plate 2162 between the holder 114 and the handheld part 12, further enclosing or covering the surface of the proximal end 1142 of the holder. The second conductor 216 can effectively shield the first conductor from the interference or noise caused by any conductor below, beside or behind (from the direction of the handheld part) the infrared thermometer 10. If the second conductor 116 is electronically connected to the microcontroller and acts as a sensor, it can sense the capacitance value of the capacitive effect from the surface of the object not desirable to be measured, for example, the user's hand holding the head 11 or the surface of a conductive table which the infrared thermometer 10 is placed on and is near the head 11.

Figure 5:
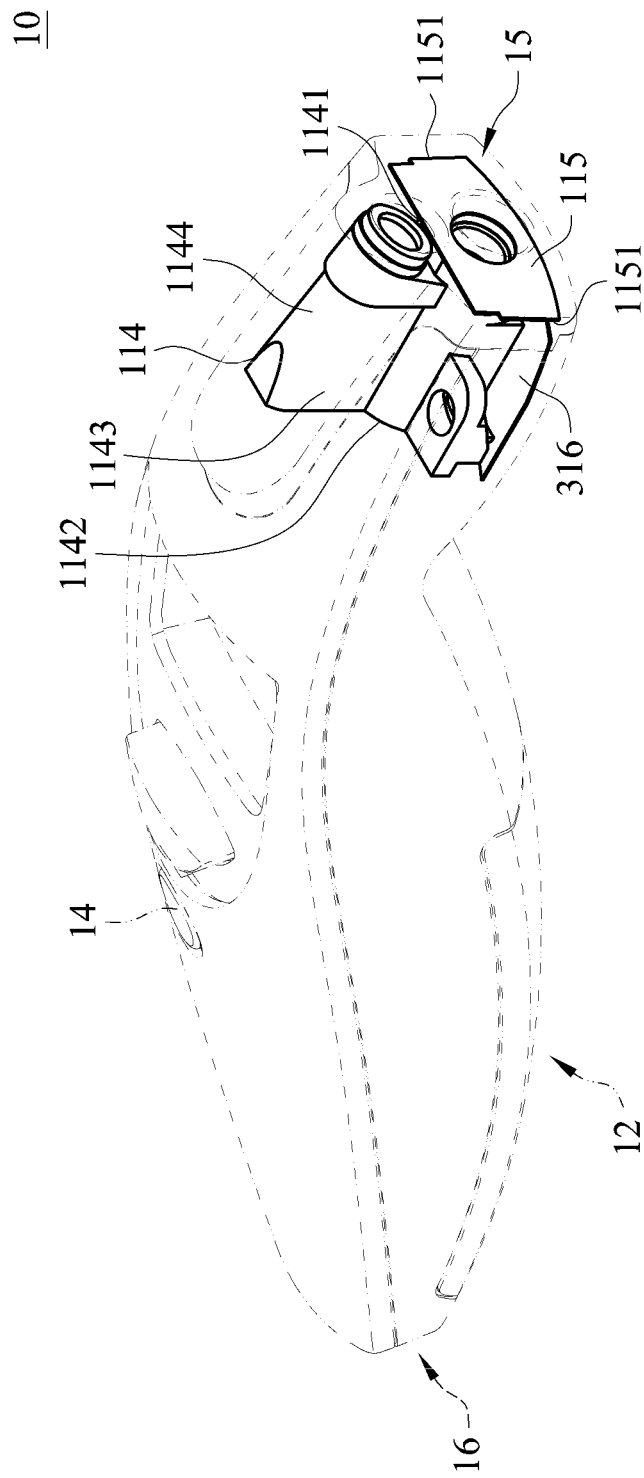
FIG. 5 is a schematic perspective view of the head of the infrared thermometer according to the third embodiment of the present invention.

In the third embodiment of the present invention, as shown in FIG. 5, in addition to the features of the present invention described above, the second conductor 316 is provided below the holder 114, proximate to the bottom surface 1145. The second conductor 316 disposed proximate to the bottom surface 1145 can effectively shield the first conductor from the interference caused by any conductor below the infrared thermometer 10.

Figure 6:
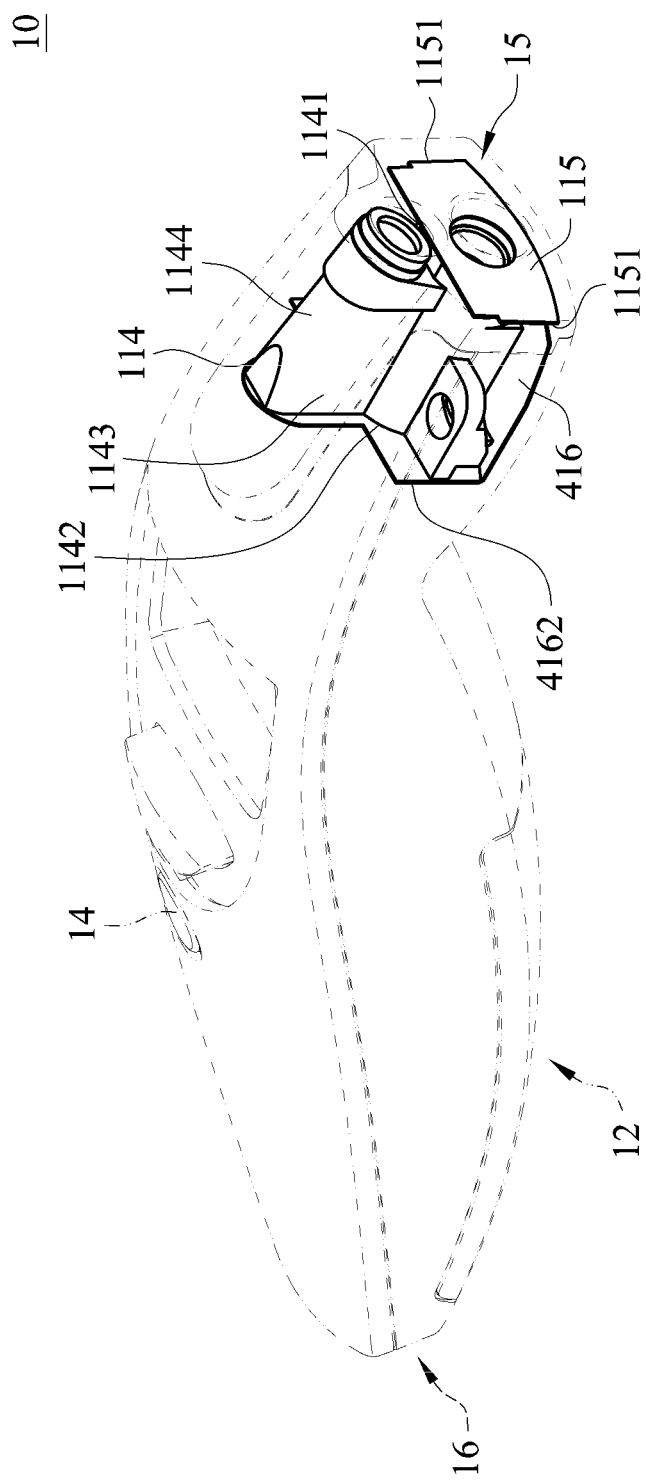
FIG. 6 is a schematic perspective view of the head of the infrared thermometer according to the fourth embodiment of the present invention.

In the fourth embodiment of the present invention, as shown in FIG. 6, in addition to the features described above and the features of the third embodiment, the second conductor 416 additionally includes an upright plate 4162 between the holder 114 and the handheld part 12, further surrounding the surface of the proximal end 1142 of the holder 114 so as to form an L-shape as viewed from the side surface of the infrared thermometer 10. The L-shaped second conductor 416 can effectively shield the first conductor from the interference caused by any conductor below and behind the infrared thermometer 10.

Figure 7:
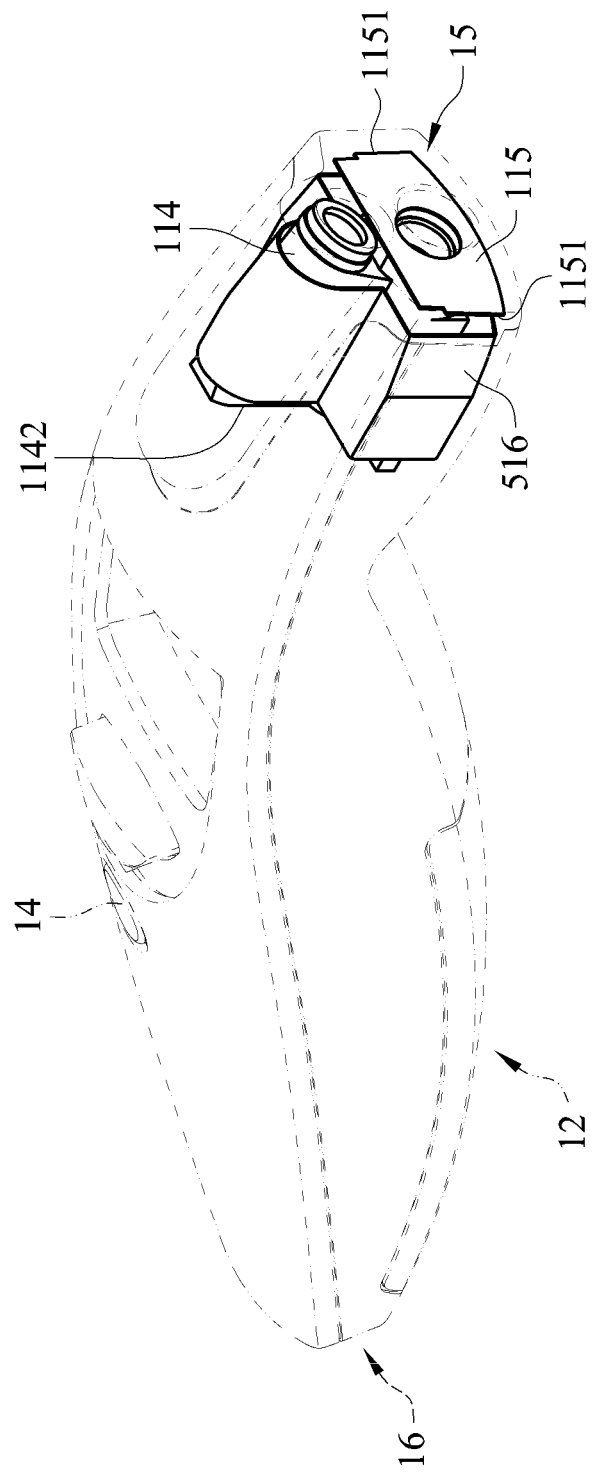
FIG. 7 is a schematic perspective view of the head of the infrared thermometer according to the fifth embodiment of the present invention.

In the fifth embodiment of the present invention, as shown in FIG. 7, in addition to the features described above, the second conductor 516 is an annular plate surrounding the side surfaces 1143, the top surface 1144 and the bottom surface 1145 of the holder 114. The second conductor 516 can effectively shield the first conductor from the interference caused by any conductors above, below, and beside the infrared thermometer 10.

Figure 8:
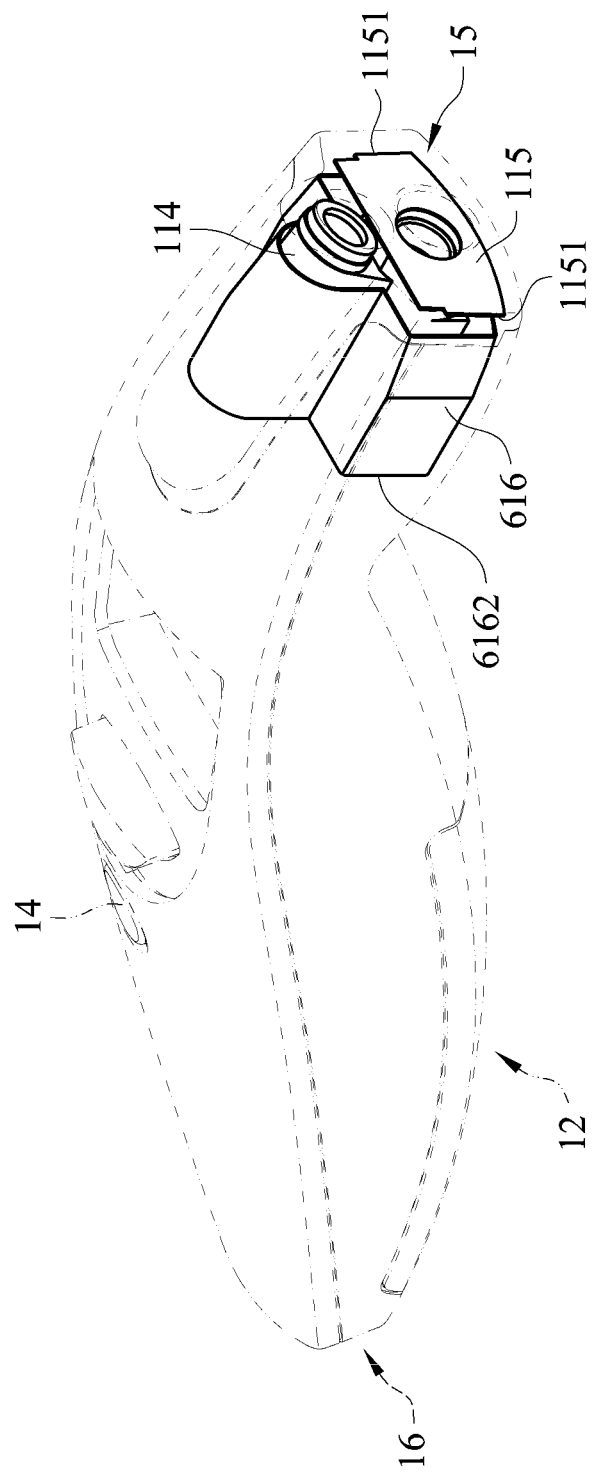
FIG. 8 is a schematic perspective view of the head of the infrared thermometer according to the sixth embodiment of the present invention.

In the sixth embodiment of the present invention, as shown in FIG. 8, in addition to the features described above and the features of the fifth embodiment, the second conductor 616 additionally includes a upright plate 6162 between the holder 114 and the handheld part 12, whereby the second conductor 616 is formed like a pocket to further enclose the surface of the proximal end 1142 of the holder. The second conductor 616 can effectively shield the first conductor from the interference caused by any conductors above, below, beside and behind the infrared thermometer 10.

Figure 9:
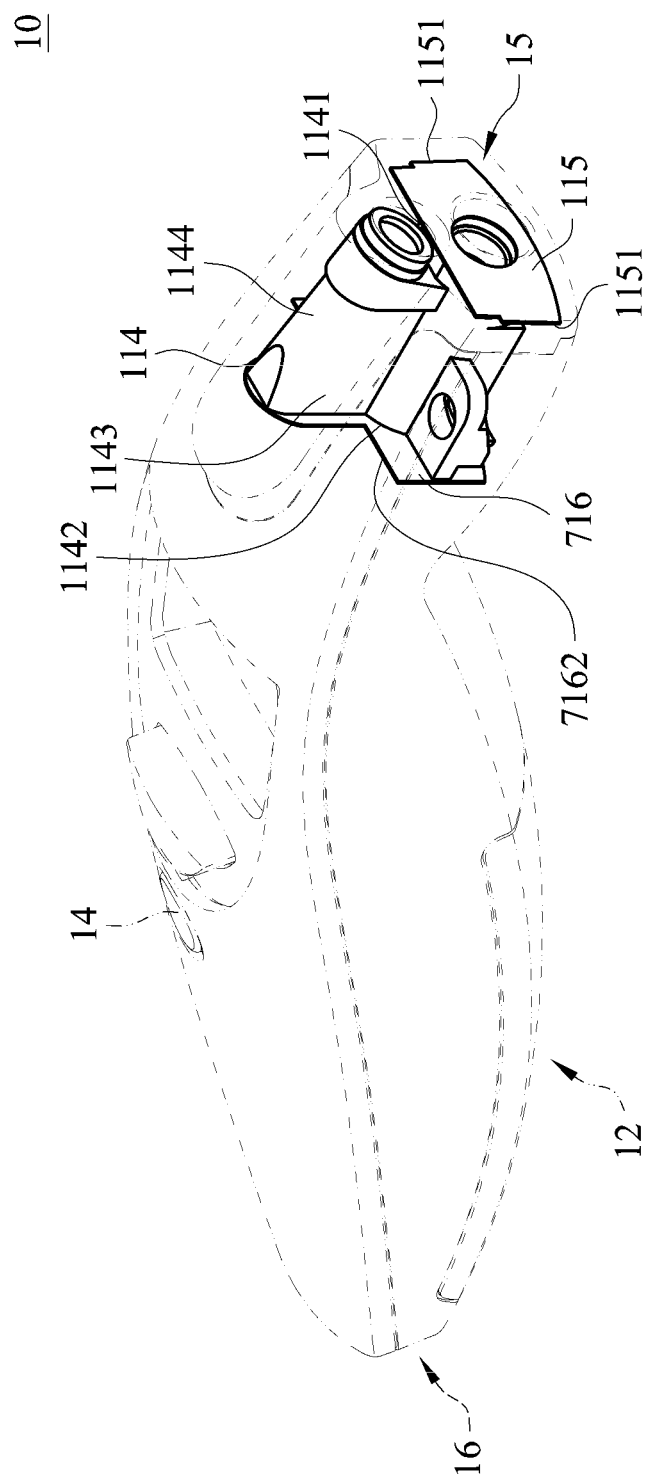
FIG. 9 is a schematic perspective view of the head of the infrared thermometer according to the seventh embodiment of the present invention.

In the seventh embodiment of the present invention, as shown in FIG. 9, in addition to the features described above, the second conductor 716 is an upright plate 7162 between the holder 114 and the handheld part 12, being opposite to the first conductor 115. In other words, the first conductor 115 is proximate to the distal end 1141 of the holder and the second conductor 716 is proximate to the proximal end 1142 of the holder. The second conductor 716 can effectively shield the first conductor from the interference caused by the conductor behind the infrared thermometer 10.

Figure 10:
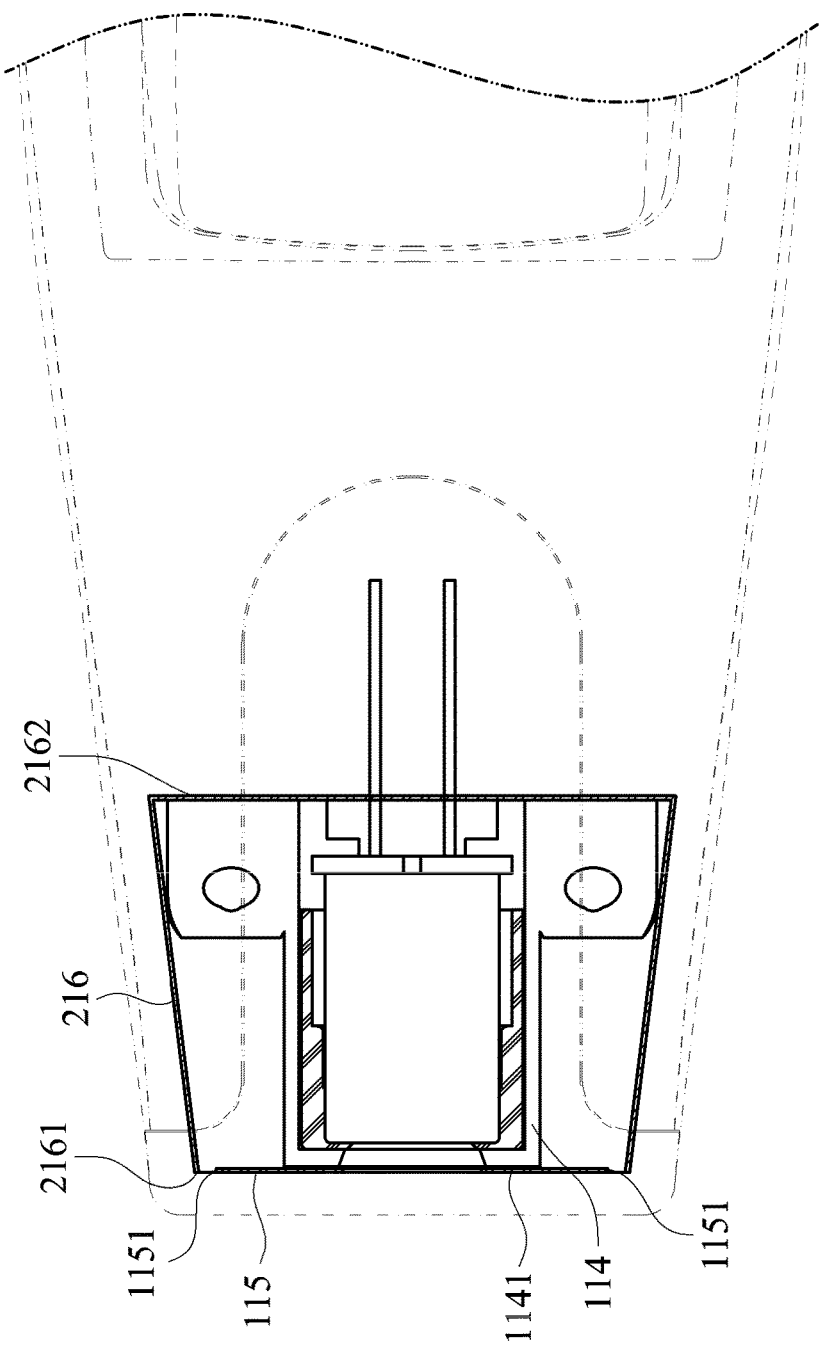
FIG. 10 is a longitudinal sectional view taken along the line A-A in FIG. 4.

FIG. 10 is a longitudinal sectional view along the A-A line of FIG. 4, illustrating the positional relationship between the second conductor 216 and the first conductor 115 in the second embodiment of the present invention. In the other embodiments, the second conductors 116, 316, 416, 516, 616 and the first conductor 115 may also have this relationship with variation. The distal edge 2161 of the second conductor 216 may be flush with the side edge 1151 of the first conductor 115, resulting in a better shielding effect of the second conductor 216 or better effect for sensing capacitance, but the present invention is not so limited as long as the edge of the second conductor at the distal end does not extend beyond the side edge 1151 of the first conductor 115.

Turning again to FIG. 2, the head 11 of the present invention further includes a housing 111 and a bottom shell 112. The housing 111 accommodates the infrared sensor 113 and the holder 114, and is joined to the bottom shell 112. The housing 111 and bottom shell 112 may be joined to each other in a snap fit manner, but the present invention is not so limited. The housing 111 and the bottom shell 112 may be joined in any suitable manner, such as screw lock, groove fit, and the like. In other embodiments, the housing 111 and the bottom shell 112 of the present invention may be integrally formed, but the present invention is not so limited.

It is particularly emphasized that in all embodiments of the present invention, the first conductor 115 may be disposed between the housing 111 and the holder 114, i.e. on the inner surface 1112 of the housing 111; or may be provided on the surface of the housing away from the holder 114, i.e. on the outer surface 1111 of the housing 111. In the second and fourth embodiments of the present invention, the second conductors 216, 416 may be disposed between the bottom shell 112 and the holder 114, i.e., on the inner surface 1122 of the bottom shell 112; or may be provided on the surface of the bottom shell 112 away from the holder 114, i.e. on the distal outer surface 1121 of the bottom shell 112.

The technical contents and technical features of the present invention have been disclosed above; however, a person skilled in the art will still be able to make various alternatives and modifications that do not depart from the spirit of the invention based on the teachings and disclosures of the present invention. Accordingly, the scope of the present invention should be no way limited to those disclosed in the example, but should include various alternatives and modifications that do not depart from the invention and is covered by the following claims.

What is claimed is:

1. An infrared thermometer, comprising
a handheld part;
a head connected to the handheld part, the head comprising
   a bottom shell;
   an infrared sensor configured to measure the temperature of an object to be measured;
   a holder configured to hold the infrared sensor to the bottom shell;
   a housing configured to accommodate the infrared sensor and the holder and to be joined to the bottom shell;
   a first conductor arranged on the housing; and
   a second conductor arranged between the first conductor and the handheld part and adjacent to the holder; and
a microcontroller configured to inactivate the infrared sensor to measure the temperature based on a second signal generated by the second conductor;
wherein the first conductor is configured to detect the distance between the head and a surface of the object to be measured when the surface of the object to be measured is approaching to the head; and
wherein the second conductor reduces interference to the first conductor from a surface of any other object not to be measured when the surface of any other object not to be measured is approaching to the head.

2. The infrared thermometer according to claim 1, wherein the first conductor is arranged on an inner or outer surface of the housing.

3. The infrared thermometer according to claim 1, wherein the second conductor is a shield configured to reduce the interference to the first conductor from the surface of any other object not to be measured.

4. The infrared thermometer according to claim 1, wherein each of the first and second conductors is a conductive plate.

5. The infrared thermometer according to claim 1, wherein the second conductor is an upright plate between the holder and the handheld part.

6. The infrared thermometer according to claim 1, wherein the microcontroller determines the distance between the head and the surface of the object to be measured based on a first signal generated by the first conductor for activating the infrared sensor to measure the temperature.

7. The infrared thermometer according to claim 1, wherein the second conductor surrounds a bottom surface and at least one side surface of the holder.

8. The infrared thermometer according to claim 7, wherein the second conductor further comprises an upright plate between the holder and the handheld part.

9. The infrared thermometer according to claim 1, wherein the second conductor is arranged adjacent to a bottom surface of the holder.

10. The infrared thermometer according to claim 9, wherein the second conductor further comprises an upright plate between the holder and the handheld part.

11. The infrared thermometer according to claim 1, wherein the second conductor is an annular plate surrounding bottom, side and top surfaces of the holder.

12. The infrared thermometer according to claim 11, wherein the second conductor further comprises an upright plate between the holder and the handheld part.

* * * * *